United States Patent [19]
Thorne et al.

[11] Patent Number: 6,036,675
[45] Date of Patent: Mar. 14, 2000

[54] SAFETY STERILE CARTRIDE UNIT APPARATUS AND METHODS

[75] Inventors: Gale H. Thorne, Bountiful; David L. Thorne, Kaysville, both of Utah

[73] Assignee: Specialized Health Products, Inc., Bountiful, Utah

[21] Appl. No.: 09/243,761

[22] Filed: Feb. 3, 1999

[51] Int. Cl.$^7$ .................................................. A61M 5/00
[52] U.S. Cl. ........................... 604/232; 604/110; 604/181; 604/187; 604/192; 604/221; 128/919
[58] Field of Search ......................... 604/110, 181, 604/187, 192, 198, 218, 228, 200, 201, 232, 234, 263, 221; 128/919

[56] References Cited

U.S. PATENT DOCUMENTS

| | | |
|---|---|---|
| 2,904,043 | 9/1959 | Friedman . |
| 3,158,155 | 11/1964 | Myerson et al. . |
| 3,848,593 | 11/1974 | Baldwin . |
| 4,112,945 | 9/1978 | Helixon et al. . |
| 4,931,040 | 6/1990 | Haber et al. .................... 604/110 |
| 4,950,249 | 8/1990 | Jagger et al. ..................... 604/192 |
| 5,135,509 | 8/1992 | Olliffe ................................ 604/192 |
| 5,139,489 | 8/1992 | Hollister ............................ 604/192 |
| 5,147,303 | 9/1992 | Martin ............................... 604/110 |
| 5,154,285 | 10/1992 | Hollister ............................ 206/365 |
| 5,193,552 | 3/1993 | Columbus et al. ................ 128/760 |
| 5,246,428 | 9/1993 | Falknor ............................. 604/198 |
| 5,254,099 | 10/1993 | Kuracina et al. ................. 604/198 |
| 5,256,153 | 10/1993 | Hake ................................. 604/198 |
| 5,348,544 | 9/1994 | Sweeney et al. ................. 604/192 |
| 5,350,367 | 9/1994 | Stiehl et al. ...................... 604/232 |
| 5,356,392 | 10/1994 | Firth et al. ........................ 604/198 |
| 5,374,255 | 12/1994 | Nathan et al. .................... 604/192 |
| 5,403,283 | 4/1995 | Luther .............................. 604/164 |
| 5,437,647 | 8/1995 | Firth et al. ........................ 604/110 |
| 5,451,214 | 9/1995 | Hajishoreh ....................... 604/235 |
| 5,480,385 | 1/1996 | Thorne et al. .................... 604/110 |
| 5,487,734 | 1/1996 | Thorne et al. .................... 604/195 |
| 5,490,841 | 2/1996 | Landis .............................. 604/110 |
| 5,542,927 | 8/1996 | Thorne et al. .................... 604/110 |
| 5,549,708 | 8/1996 | Thorne et al. .................... 604/110 |
| 5,573,510 | 11/1996 | Isaacson ........................... 604/158 |
| 5,584,816 | 12/1996 | Gyure et al. ..................... 604/192 |
| 5,669,889 | 9/1997 | Gyure et al. ..................... 604/263 |
| 5,695,477 | 12/1997 | Sfikas ............................... 604/241 |
| 5,733,265 | 3/1998 | Bachman et al. ................ 604/263 |
| 5,746,726 | 5/1998 | Sweeney et al. ................. 604/263 |
| 5,823,997 | 10/1998 | Thorne ............................. 604/110 |
| 5,913,846 | 6/1999 | Szabo ............................... 604/263 |
| 5,993,426 | 11/1999 | Hollister .......................... 604/192 |

FOREIGN PATENT DOCUMENTS

WO90/01348  2/1990  WIPO .

*Primary Examiner*—Corrine McDermott
*Assistant Examiner*—Cris L. Rodriguez
*Attorney, Agent, or Firm*—Gale H. Thorne

[57] ABSTRACT

A low cost safety sterile cartridge injector apparatus comprising an injector and a safety needle sheath having elements which promote facile assembly and disassembly. An embodiment is disclosed which incorporates an integral needle hub and safety sheath which is displaced to protectively cover a medical needle after use. The sheath also incorporates patterns of rachet teeth which cooperate with a holder portion of the injector to lock a sterile cartridge in place for use in a medical procedure and to release the cartridge for facile disposal when the sheath is displaced to cover and protectively shroud the needle after use. Through this process, need for rotary collars to capture and hold the cartridge in place during use is eliminated, reducing injector cost and apparatus assembly steps and time.

20 Claims, 12 Drawing Sheets

SAFETY STERILE CARTRIDE UNIT APPARATUS AND METHODS

FIELD OF INVENTION

This invention is generally related to safety medical needle devices and particularly to medical needle protective devices used as injectors for unit-dose sterile cartridge syringe products.

DESCRIPTION OF RELATED ART

Unit-dose sterile cartridge systems are well known in the medical arts. Currently, two of the most common types of unit-dose cartridges for which injectors are used are the Tubex® cartridge unit, available through Wyeth-Ayerst Laboratories, Philadelphia, Pa. 19101, and the Carpuject® unit-dose sterile cartridge available through Abbott Laboratories, North Chicago, Ill. 60064.

It is widely published in the United States that, in 1992, six billion medical needles were used annually in a broad range of medical procedures in the U.S. alone. Approximately two-thirds of those six billion medical needles were used in applications which do not directly involve direct, patient related needle sticks. For those applications, needle free or blunted point systems, examples of which are Abbott Laboratories' LifeShield® Prepierced Reseal Injection Site and Baxter Laboratories' Interlink® systems are used.

While such needle free systems have, with varying degrees of success, addressed a majority of occurrences of accidental needle sticks, the remaining minority (approximately two million) are the basis of substantially more dangerous needle sticks, for the needle free systems address points of communication which are removed from a patient and the more dangerous accidental needle sticks are by sharps or needles which are contaminated by direct contact, usually associated with percutaneous entry, with the patient.

Currently, needle free systems are available for both the Tubex and Carpuject systems, but there are no known safety devices for needles used in direct-needle-entry applications. The inventors believe the danger and, therefore, the need for finding a solution which improves safety when using a needle for percutaneous needle entry is far greater for direct-needle-entry procedures.

There are many types of needle protection devices in the needle and medical syringe safety art. These types include devices which retract a needle into a protective sheath, devices which extend a sheath to surround a needle and devices comprising sheaths which are manually disposed about a needle to provide protection. Most of these types are effective when protectively disposed about a needle, but, in many cases, are generally ineffective due to inconvenience of displacing the sheaths to activate a protective state and commercially unsuccessful due to cost and complexity of making such devices.

BRIEF SUMMARY AND OBJECTS OF THE INVENTION

In brief summary, this novel invention alleviates all of the known problems related to providing protection from a needle which has been contaminated by percutaneous entry or other direct patient contact. Devices based upon the instant invention are considered by the inventors to be inherently safe and effective and promise to be cost effective in many forms. In addition, apparatus, based upon the invention, simplifies assembly of a cartridge into an injector and removal of the cartridge from the injector after the contaminated needle has been disposed within a protective sheath. The assembly of the cartridge into the injector requires fewer steps than contemporary sterile cartridge systems. Further, the invention does not permit disassembly of the needle and cartridge from the injector until the needle is so safely disposed. As a point of novelty, activation of the device to safely sheath the needle also initiates a release which facilitates disassembly of the cartridge and needle from the injector.

The invention permits use of standard, contemporarily available sterile cartridges. The injector comprises but two parts, a plunger rod and a cartridge holder. (Contemporary injectors are generally combinations of three parts, including a plunger rod, a cartridge holder and a rotary member for securing the cartridge to the holder.) Sheath mechanisms of the invention are generally associated with an integral medical needle and cartridge-interfacing needle hub or alternatively with a separate cartridge interfacing hub which in turn is interconnected to a standard medical needle through a medical connection, such as a Luer or Luer-lock fitting.

For use as a safety shroud, the sheath is preferably moveable from latent, out of the way, disposition, relative to needle use, to a position where it provides a protective safety cover for the needle. A primary element of the invention is the provision for facile assembly and disassembly of the injector, cartridge and medical needle before and after use, respectively.

For assembly, the sheath and associated hub are linearly displaced into connective interfaces between the cartridge holder and sheath to effect a secure connection between an associated medical needle hub and the cartridge holder and between the medical needle hub and cartridge to thereby firmly affix the cartridge within the holder for the purpose of providing a liquid communicating channel between the cartridge and medical needle hub. If a separate hub and medical needle combination is used, the medical needle may be affixed to the hub as a subsequent step in assembly. Of course, as is standard connecting procedure, the plunger rod is threadably engageable with a plunger in the cartridge.

Preferably, a prerequisite for disassembly is protective displacement of the sheath about the needle. For this reason, displacement of the sheath also disengages the connective interface between the holder and sheath permitting easy disassembly.

In a preferred embodiment, the sheath is displaced pivotally to protectively shroud the needle. The holder comprises a pair of distally extending arms having a series of internally disposed ratchet teeth which cooperate with a pair of associated patterns comprising corresponding sets of oppositely disposed ratchet teeth, disposed on external faces of the sheath to firmly affix the holder to the sheath when the sheath is displaced into a latent state, thereat. Because the sheath is pivotally displaced to effect a covering safety shroud over the needle, each corresponding set of ratchet teeth preferably comprises a circular pattern, the radii of which are defined by the relative rotational displacement of the pivoting sheath, to maintain a firm connection between the internally disposed and externally disposed ratchet teeth while the sheath is being displaced to cover the needle.

At a point where the needle is safely shrouded, the sheath is latched to firmly secure the shield in place. At this point, the patterns, then juxtaposed to the arms, are blanked with the ratchet teeth removed. So disposed, the needle is protected and the needle and cartridge are disengaged for facile removal of the shrouded needle and associated cartridge from the holder by simply unthreading the plunger rod from the plunger and sliding the covered needle and cartridge away from the holder. It should be noted that the act of affixing the hub to the cartridge, which is disposed in the holder, simultaneously releasibly, but securely, affixes the sheath to the holder, thereby bypassing the earlier mentioned operation, by devices of previously mentioned art, of a rotary member to affix the cartridge within a holder.

Accordingly, it is a primary object to provide a safety sterile cartridge injector apparatus comprising an injector and a needle safety mechanism.

It is an important object to provide an injector and needle safety mechanism which is compatible with at least one commercially available sterile cartridge.

It is an object to provide an apparatus to provide apparatus which is compatible with a sterile cartridge assembly method which does not require a rotary member to affix the cartridge within a holder.

It is a very important object to provide an apparatus which permits (1) a secure linear connection, between a needle safety mechanism and the injector apparatus, to be made when assembling the apparatus with a sterile cartridge, (2) activation of a needle safety mechanism while the connection is retained and (3) a subsequent release of the connection after the safety mechanism is activated.

It is an object to provide a hub assembly for the apparatus which is molded as an integral part with the safety mechanism.

It is an important object to provide an injector which consists of a plunger rod and a sterile cartridge holder.

These and other objects and features of the present invention will be apparent from the detailed description taken with reference to accompanying drawings.

DETAILED DESCRIPTION OF THE ILLUSTRATED EMBODIMENTS

In this description, the term proximal is used to indicate nearness of a segment of a device or an object of a sentence relative to a clinician or user of the device. Conversely, the term distal is used to indicate farness of a segment of a device or an object of a sentence relative to the clinician or user of the device. Reference is now made to the embodiments illustrated in FIGS. 1–12 wherein like numerals are used to designate like parts throughout.

Figure 1:
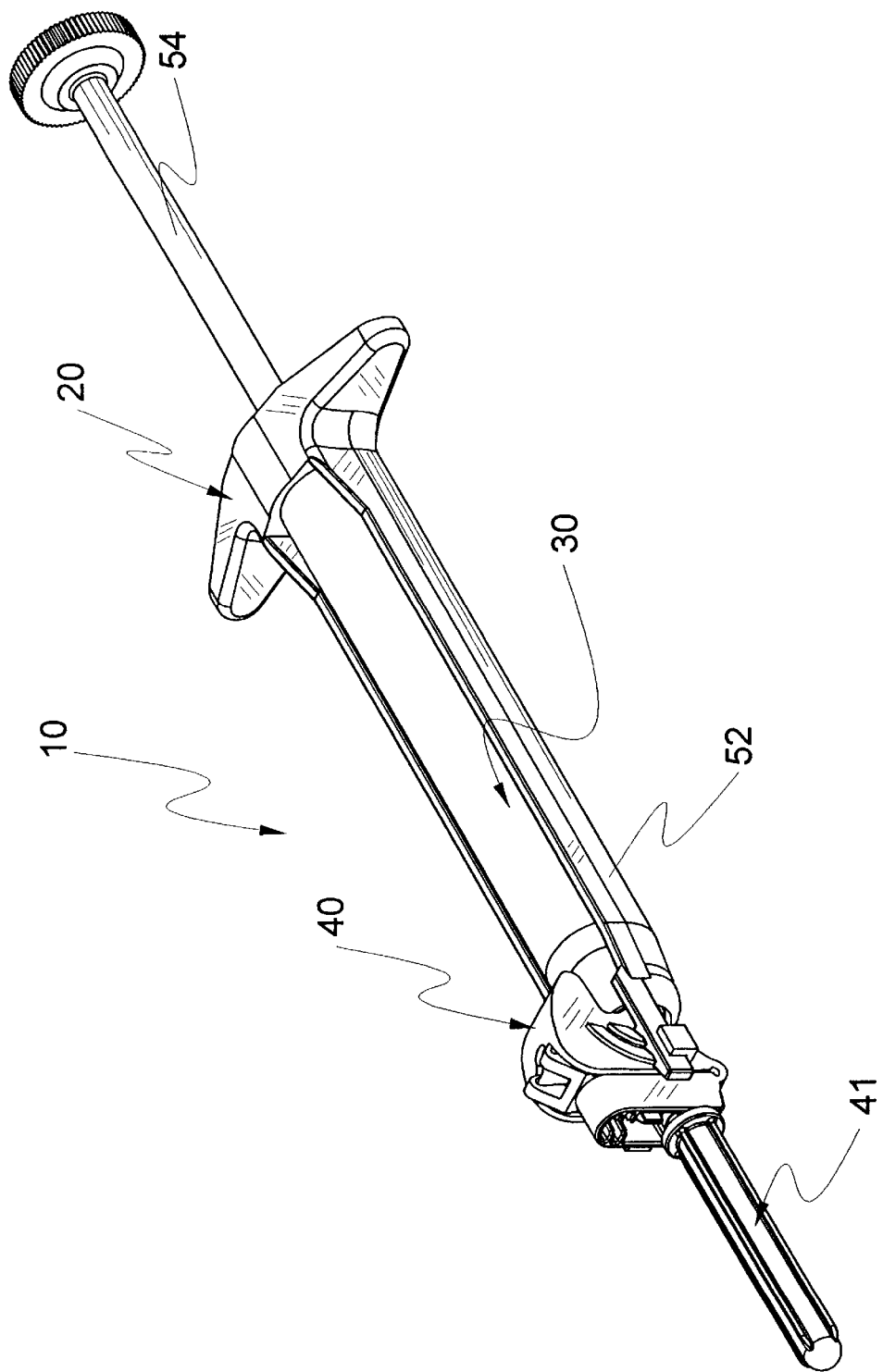
FIG. 1 is a perspective of a device according to the invention as assembled prior to use, the device being seen to comprise a holder, a sterile cartridge, a medical needle hub assembly with a medical needle and a safety sheath affixed thereto and a needle cover.

As seen in FIG. 1, a device 10, which complies with the instant invention and as assembled prior to use, comprises a holder 20, a sterile cartridge 30 and a medical needle hub assembly 40. A needle cover 41 is affixed to device 10 and disposed to provide cover and protection for a sharpened point of a medical needle.

Figure 2:
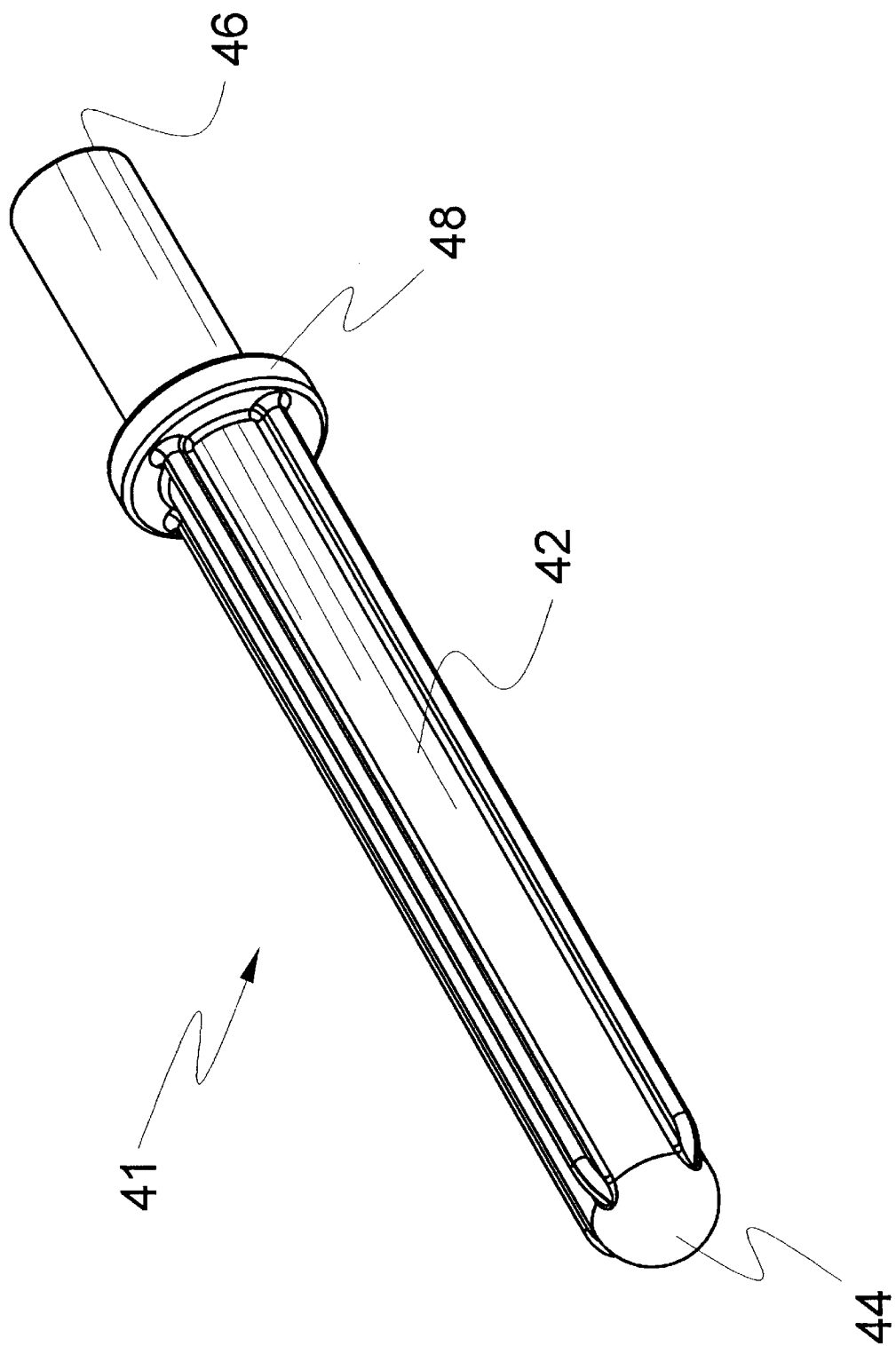
FIG. 2 is a magnified perspective of the needle cover.

As seen in FIG. 2, needle cover 41 comprises a long, hollow tubular shaft 42 closed at a distal end 44 and an open needle receiving proximal end 46. Further cover 41 comprises a medially disposed raised ring 48 which communicates with an abutting portion of medical needle hub assembly 40 to permit the medical needle assembly 40 and sterile cartridge 30 to be forcibly and securely engaged with holder 20 as seen in FIG. 1. Such covers as cover 41 are commonly used in medical applications and are commonly injection molded from polypropylene. Once needle hub assembly 40 is engaged with holder 20, cover 41 may be removed to provide access to a medical needle 50 and its sharpened tip 51 as seen in FIG. 3.

Figure 3:
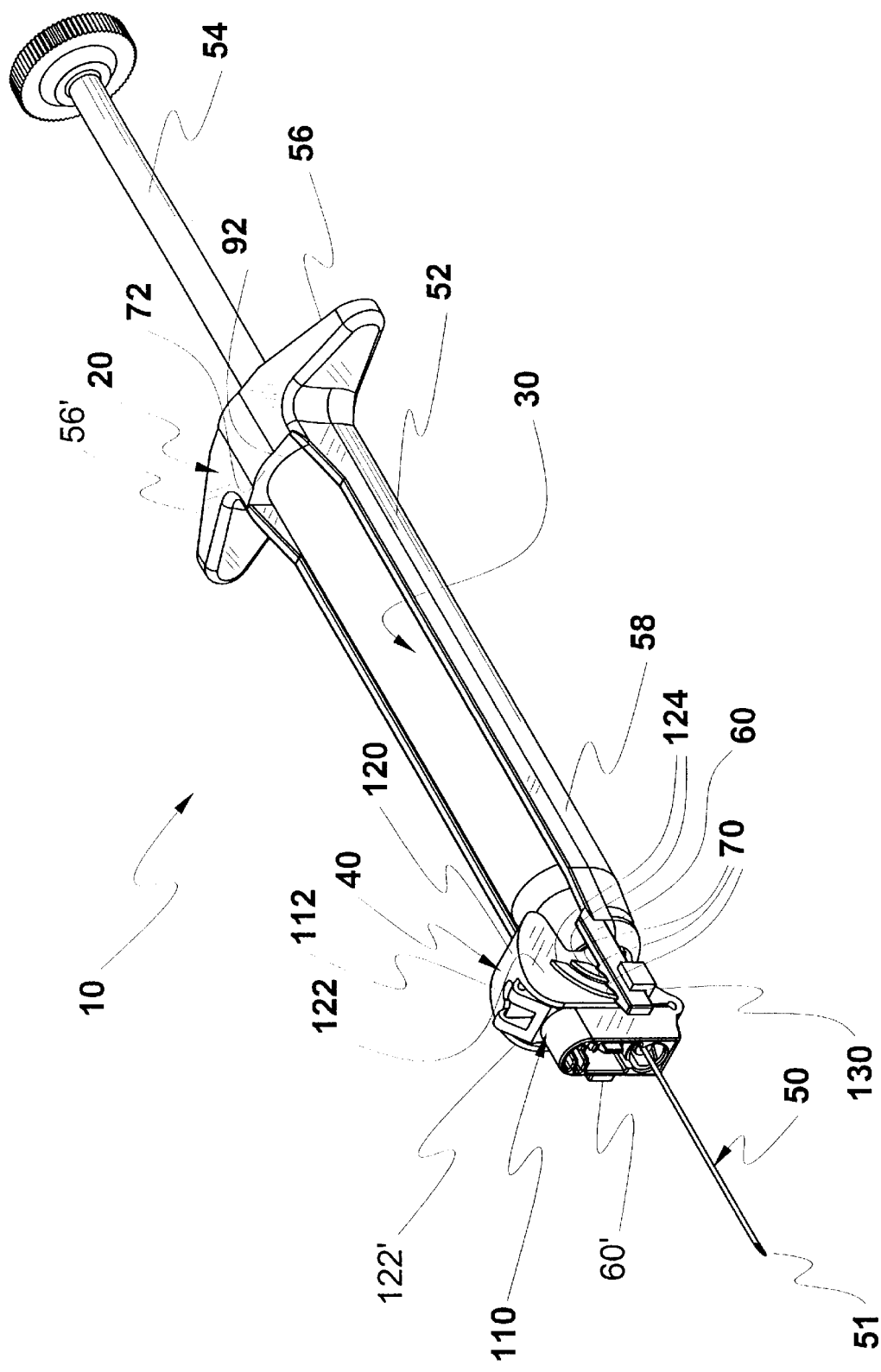
FIG. 3 is a perspective of the device prepared for use by removing the needle cover.
Figure 6:
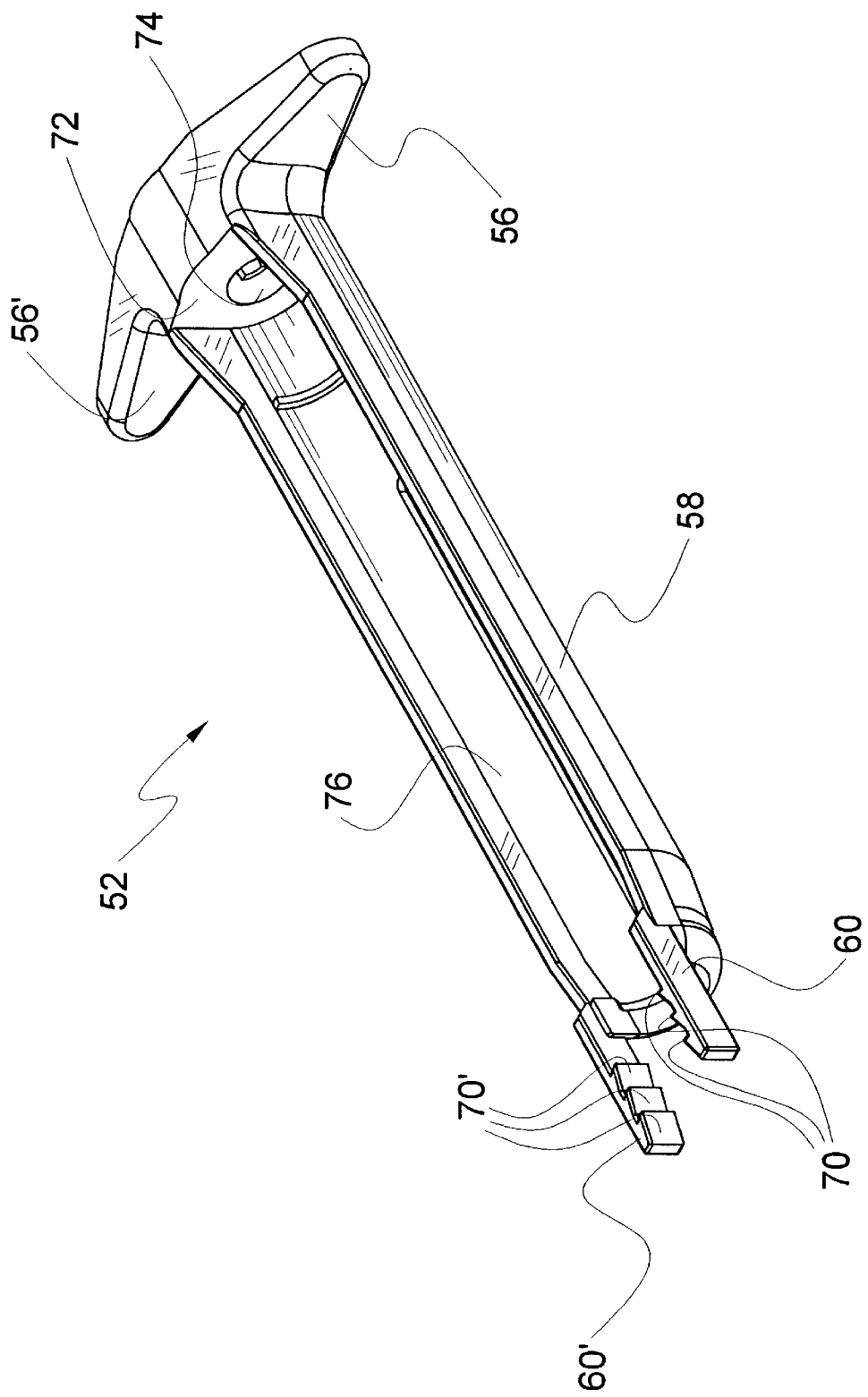
FIG. 6 is a magnified perspective of a housing tray portion of the holder.

Holder 20 comprises but two major parts, a sterile cartridge container 52 and a plunger rod 54, as seen in FIGS. 1 and 3. As seen in FIG. 6, container 52 comprises a pair of laterally extending, proximally disposed handles 56 and 56' for gripping device 10 when used as a syringe, an elongated cartridge tray 58 and a pair of distally extending arms 60 and 60'. Arms 60 and 60' each comprise a plurality of medially disposed ratchet teeth, generally numbered 70 and 70', respectively. Medially disposed relative to handles 56 and 56' is an abutment 72 comprising a through hole 74. Cartridge tray 58 comprises a convex cradle 76 wherein a sterile cartridge 30 is disposed for use in a medical procedure. Cartridge container 52 may be injection molded from a synthetic resinous material such as a medical grade polycarbonate.

Figure 7:
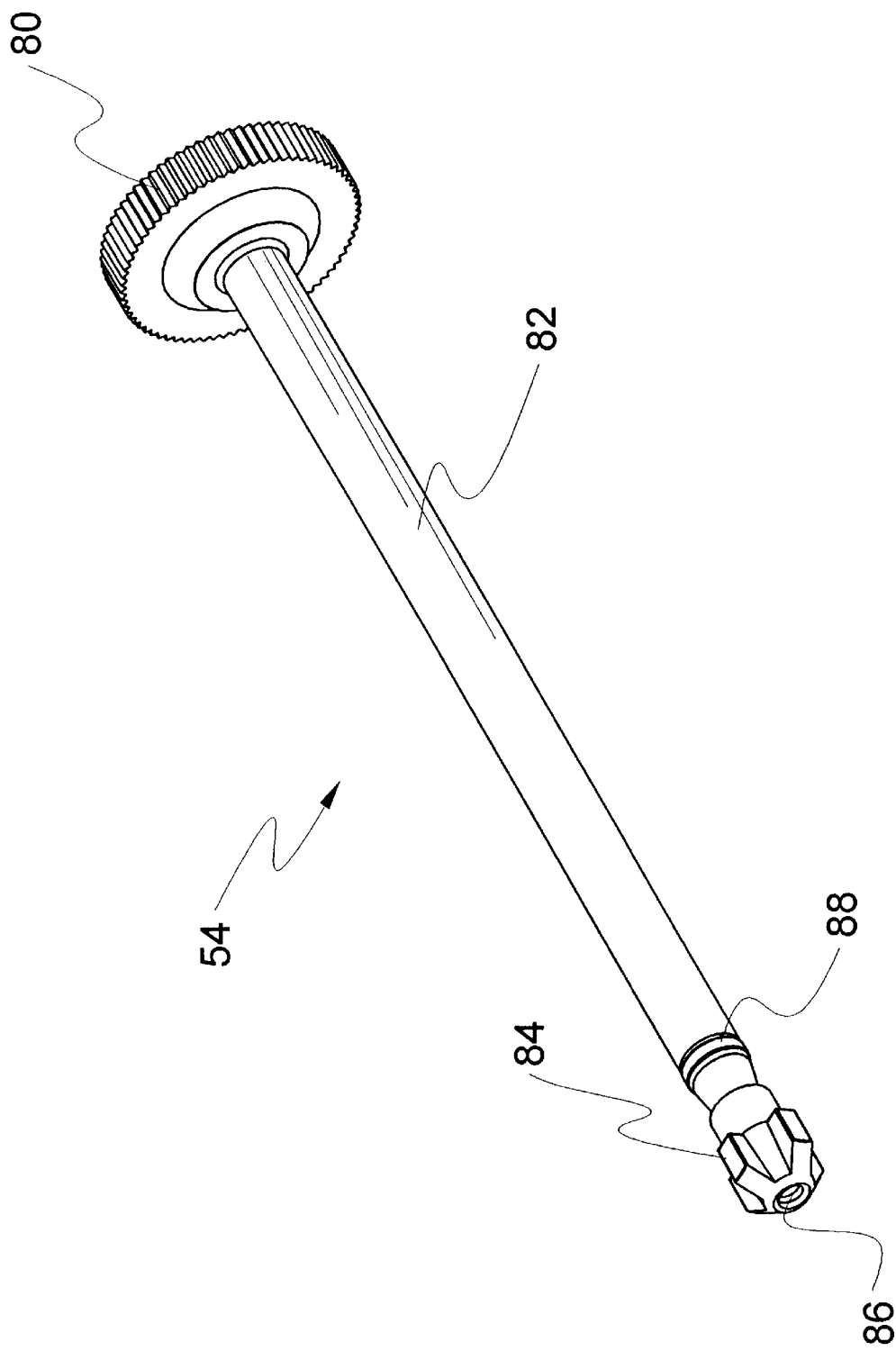
FIG. 7 is a magnified perspective of a plunger rod portion of the holder.

As is seen in FIG. 7, plunger rod 54 comprises a proximally disposed disk shaped actuator 80, an elongated circular rod 82 and a distally disposed connector knob 84. Knob 84 comprises a threaded female connection 86, the purpose for which is described in detail hereafter. Also, proximally disposed relative to knob 84, is a raised bulbous section 88 which retards separation of plunger rod 54 from container 52 after rod 82 has been forcefully inserted through hole 74. Such modes of affixing a plunger rod in a through hole is well known in the art. Plunger rod 54 may also be injection molded from synthetic resinous material such as polycarbonate.

Figure 4:
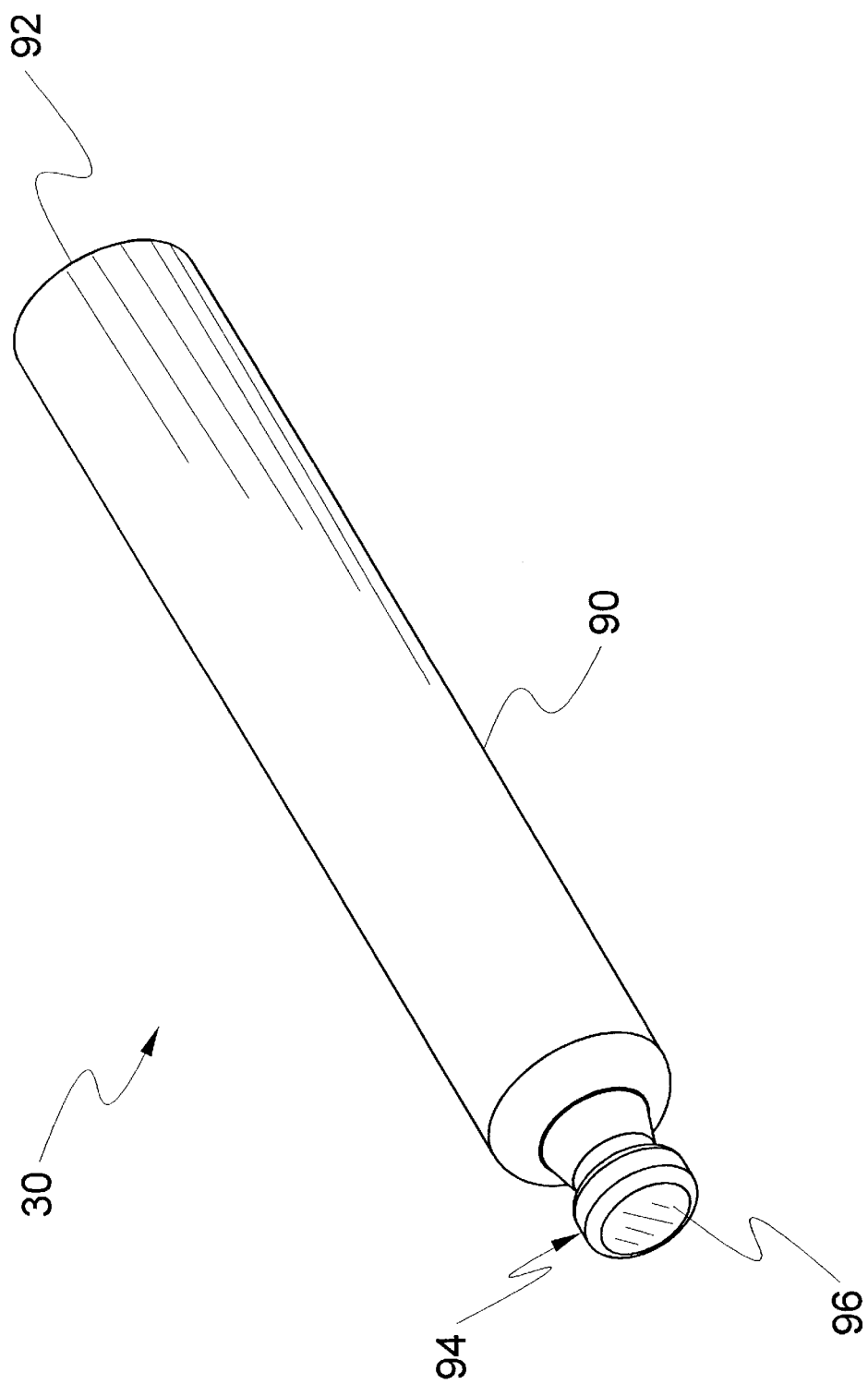
FIG. 4 is a magnified perspective of the sterile cartridge.
Figure 5:
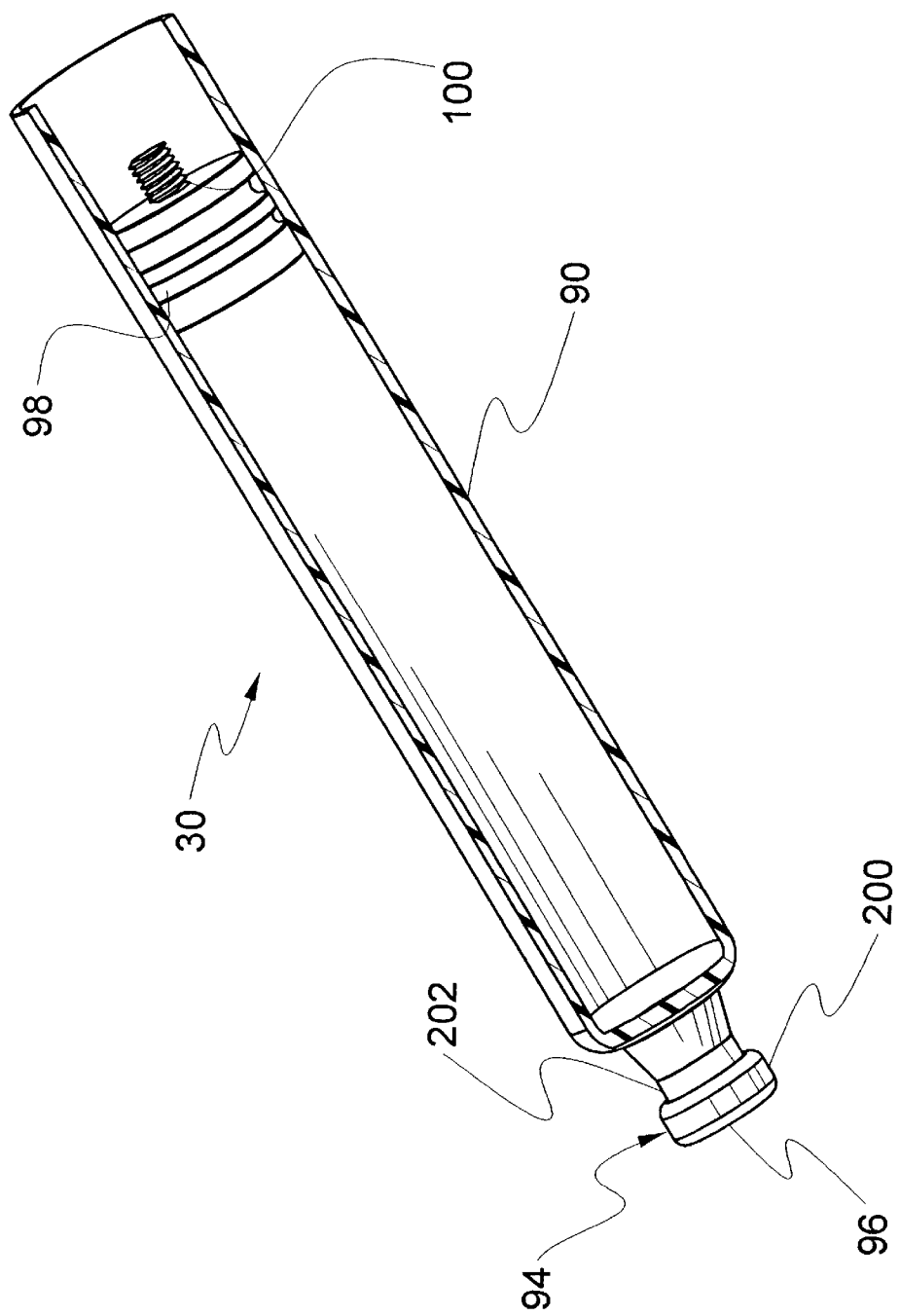
FIG. 5 is a magnified side view of the sterile cartridge of FIG. 4 with a portion removed.

A sterile cartridge container 30 is depicted in FIG. 4. Such containers are well known in the medical art, are used generally for unit dose drug injections and are presently commercially available for dispensing a wide variety of drugs. Container 30 comprises an elongated cylindrical hollow body 90 which has an open proximal end 92 and a constricted distal end 94 which is sealed with a pierce able seal 96. As seen in FIG. 5, container 30 comprises a plunger 98 which is shaped and sized to provide a sliding seal within hollow body 90. Plunger 98 comprises a threaded part 100 which is sized and shaped to cooperatively communicate with connection 86, previously referenced in FIG. 7, to releasibly affix plunger rod 54 to plunger 98. Such connections between plungers and plunger rods are commonly used in contemporary sterile container dispensing devices.

Figure 9:
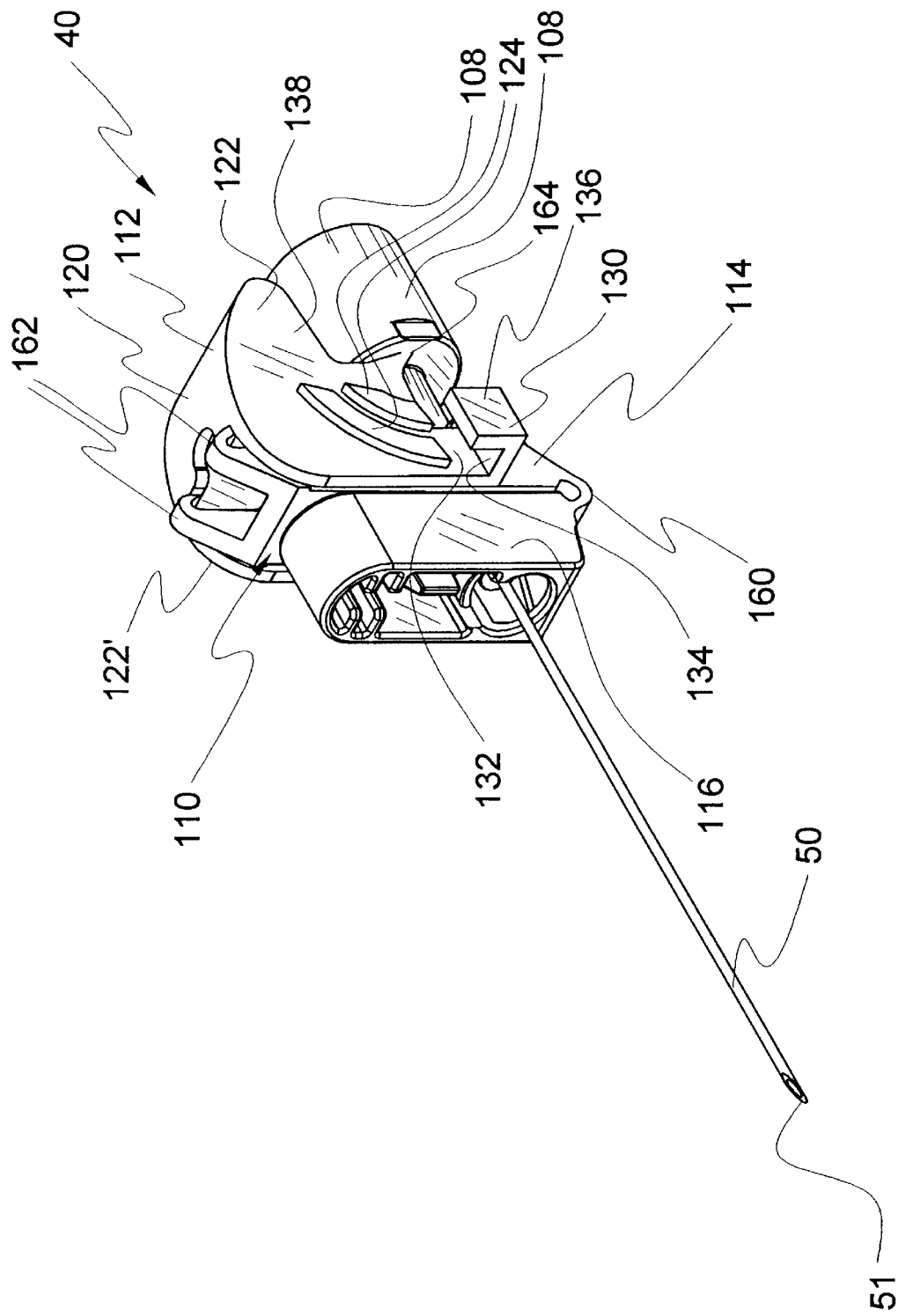
FIG. 9 is a magnified perspective of the medical needle hub assembly with the safety sheath affixed thereto.

As seen in FIGS. 3 and 9, medical needle hub assembly 40 comprises medical needle 50, a needle hub 108 and an extendable sheath and hub assembly 110. Better seen in FIG. 10, extendable sheath and hub assembly 110 comprises a plurality of parts 112, 114 and 116 interconnected by hinges which are described in detail hereafter. Part 112 is further hinged to needle hub 108, as is disclosed in detail hereafter.

Part 112 comprises a superiorly and proximally disposed sheath displacement button 120 medially disposed between a pair of juxtaposed exterior face plates 122 and 122'. An arcuate pattern 124 of ratchet teeth disposed on exterior face plate 122. Part 112 also comprises a similar set of ratchet teeth which are disposed as a mirror image of arcuate pattern 124 on oppositely disposed lateral exterior face 122', but not shown in the figures. Size and shape of the ratchet teeth of pattern 124 and that of the oppositely disposed ratchet teeth align and mesh with ratchet teeth 70 of container 52 to securely, but releasibly, affix medical needle hub assembly 40 to holder 20, as seen in FIG. 3.

Figure 10:
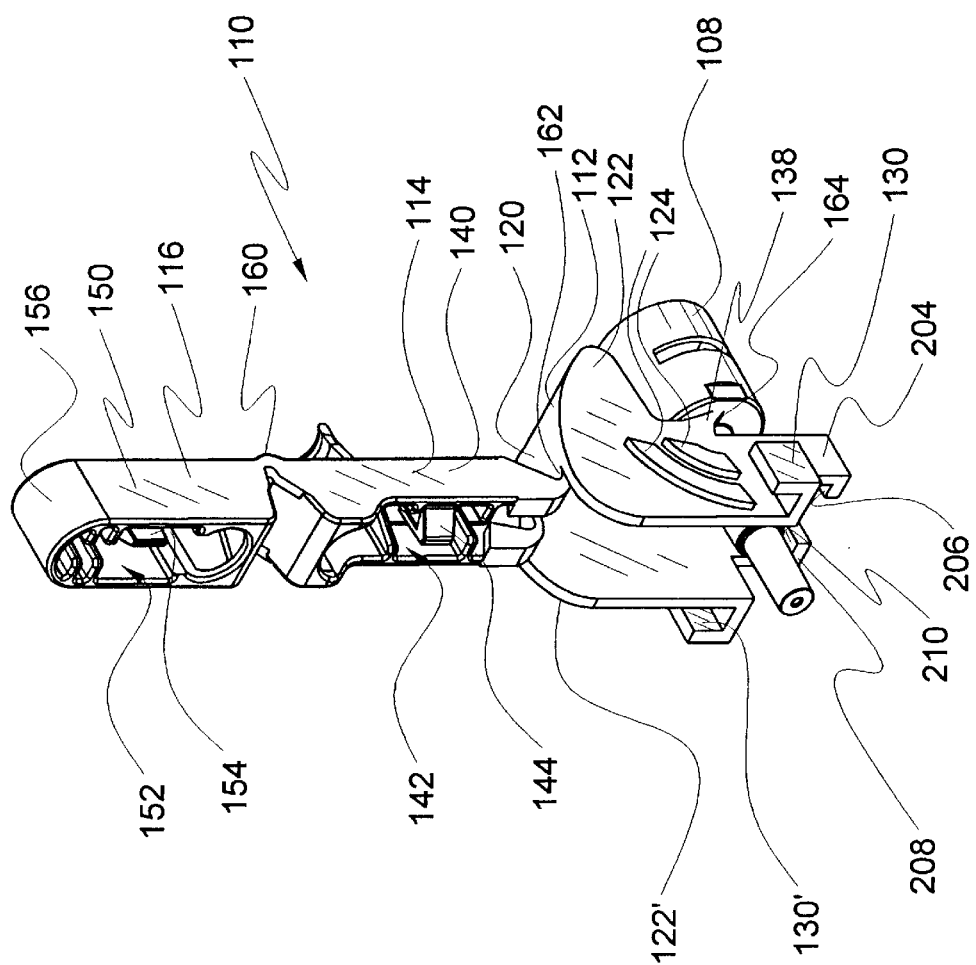
FIG. 10 is a magnified perspective of the needle hub assembly as molded and before the medical needle is affixed thereto.

Referring specifically to the orientation of medical needle hub assembly 40 in FIG. 9, Face plate 122 is seen to comprise an inferiorly disposed "U" shaped bracket 130 comprising a descending portion 132 of face plate 122, a transversely extending segment 134 and a superiorly extending portion 136 juxtaposed portion 132. Another "U" shaped bracket 130', which is similar to but disposed in mirror image fashion to "U" shaped bracket 130, is affixed to face plate 122'. "U" shaped bracket 130' is best seen in FIG. 10. Note also, in FIG. 9, that the arcuate pattern 124 of rachet teeth is abruptly proximally terminated whereat a planar area 138 provides a ratchet tooth free area.

Part 114 is also best seen in FIG. 10 which displays an 'as molded' disposition of extendable sheath and hub assembly 110 of medical needle hub assembly 40. (Note that, extendable sheath and hub assembly 110 is the same as medical needle hub assembly 40 without needle 50 being affixed to needle hub assembly 40.) Part 114 comprises an elongated housing 140 having a hollow interior 142 wherein a medical portion of needle 50 is disposed when, for safety, extendable sheath and hub assembly 110 provides a shroud about needle 50. Part 114 also comprises a needle clip 144 which securely becomes affixed to needle 50 when extendable sheath and hub assembly 110 is disposed about needle 50.

In FIG. 10, part 116 is the most superiorly disposed segment of sheath and hub assembly 110. Similar to part 114, part 116 comprises an elongated housing 150 having a hollow interior 152 in which medical needle 50 is similarly disposed. Part 116 also comprises a needle clip 154 which securely becomes affixed to needle 50 when acting as a safety sheath and a closed end 156 which provides protection for the sharpened end 51 of needle 50.

Extendable sheath and hub assembly 110 is preferably injection molded as an integral part out of a pliable synthetic resinous material, such as medical grade polypropylene. A similar safety needle sheath is disclosed and claimed in U.S. Pat. No. 5,823,997, issued Oct. 20, 1998 to David L. Thorne (Thorne). Consistent with the disclosure in Thorne, part 116 is foldably interconnected to part 114 via a living hinge 160. Likewise part 114 is interconnected to part 112 by means of a living hinge 162. More important and more critical to operation of the instant invention, part 112 is pivotally connected to needle hub 108 by a living hinge 164. Though not specifically required for the invention disclosed herein, sheaths, such as those disclosed in Thorne, are particularly applicable to the instant invention as a part to which a ratcheting mechanism, such as ratchet teeth of arcuate pattern 124, may be added such that the ratcheting mechanism is pivotally displaced then the sheath is disposed to safely shield a medical needle, such as needle 50.

As disclosed heretofore, extendable sheath and hub assembly 110 are preferably formed as an integrally molded part. Even so, a needle hub 108 and an associated needle 50 is seen as a separate item in FIG. 8 for clarity of disclosure. Proximally, needle hub 108 comprises a hollow cylindrical section 170. Section 170 comprises a distally disposed end 172 which is closed except for an open orifice 174 through which a proximal portion 176 of needle 50 is exposed. Extending proximally from end 172, section 170 comprises a cylindrical solid of revolution which is sized and shaped to fit snugly about distal end 94 of container 30. (See FIG. 4.) Portion 176 of needle 50 comprises a proximally disposed sharpened tip 178 and exposure to a lumen 180 of needle 50. Tip 178 pierces seal 96 as distal end 94 is displaced to reside within section 170, thereby providing a communicating pathway for contents of container 30 into lumen 180.

Referring once more to FIG. 1, it may be noted that a container 30 and a needle hub assembly 40 may be linearly displaced (slid) into holder 20 while cover 41 is disposed to safeguard needle 50 and its sharpened point 51. Of course, container 30 and needle hub assembly 40 may be sequentially displaced, separately, into holder 20, as well. As seen in FIG. 3, proximal end 92 of container 30 is proximally displaced until it contacts abutment 72. Needle hub assembly 40 is proximally displaced until needle tip 178 pierces seal 96 and distal end 94 fits well within cylindrical section 170. (For reference, see FIGS. 4 and 8.) As such displacement occurs, pattern 124 (and similar pattern on faceplate 122') of ratchet teeth become juxtaposed ratchet teeth 70 (and 70', respectively). Simultaneously, "U" shaped brackets 130 and 130' are disposed about arms 60 and 60', respectively to stabilize container 30 and needle hub assembly 40 against upward vertical displacement relative to carrier 20. Note that downward vertical displacement is inhibited by cradle 76 (see FIG. 6) of cartridge tray 58. Lateral displacement is inhibited by arms 60 and 60' which are sized and positioned to contact opposing face plates 122 and 122', respectively. Displacement in line with the long axis of needle 50 is restricted proximally by interaction of abutment 72 and proximal end 92 and distally by interaction of pattern 124 (and similar pattern on faceplate 122') of ratchet teeth and ratchet teeth 70 and 70', respectively.

Figure 11:
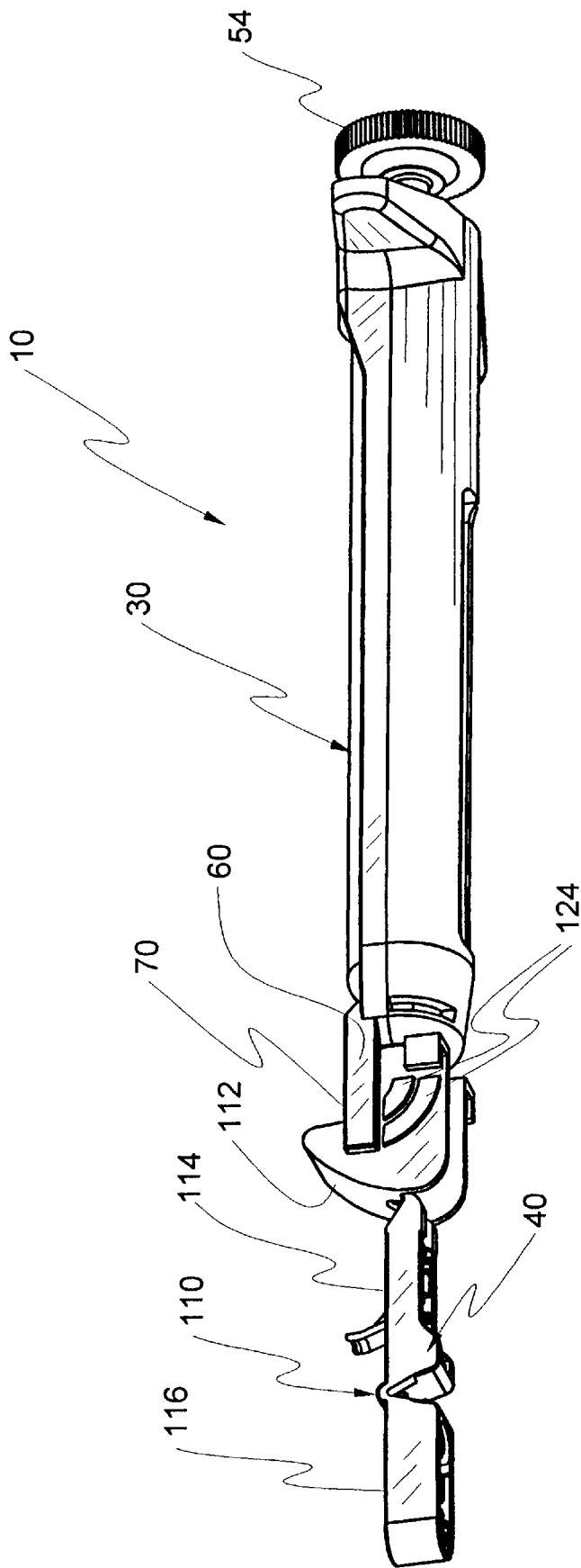
FIG. 11 is a perspective of the device with the safety sheath disposed to protectively cover the medical needle.
Figure 12:
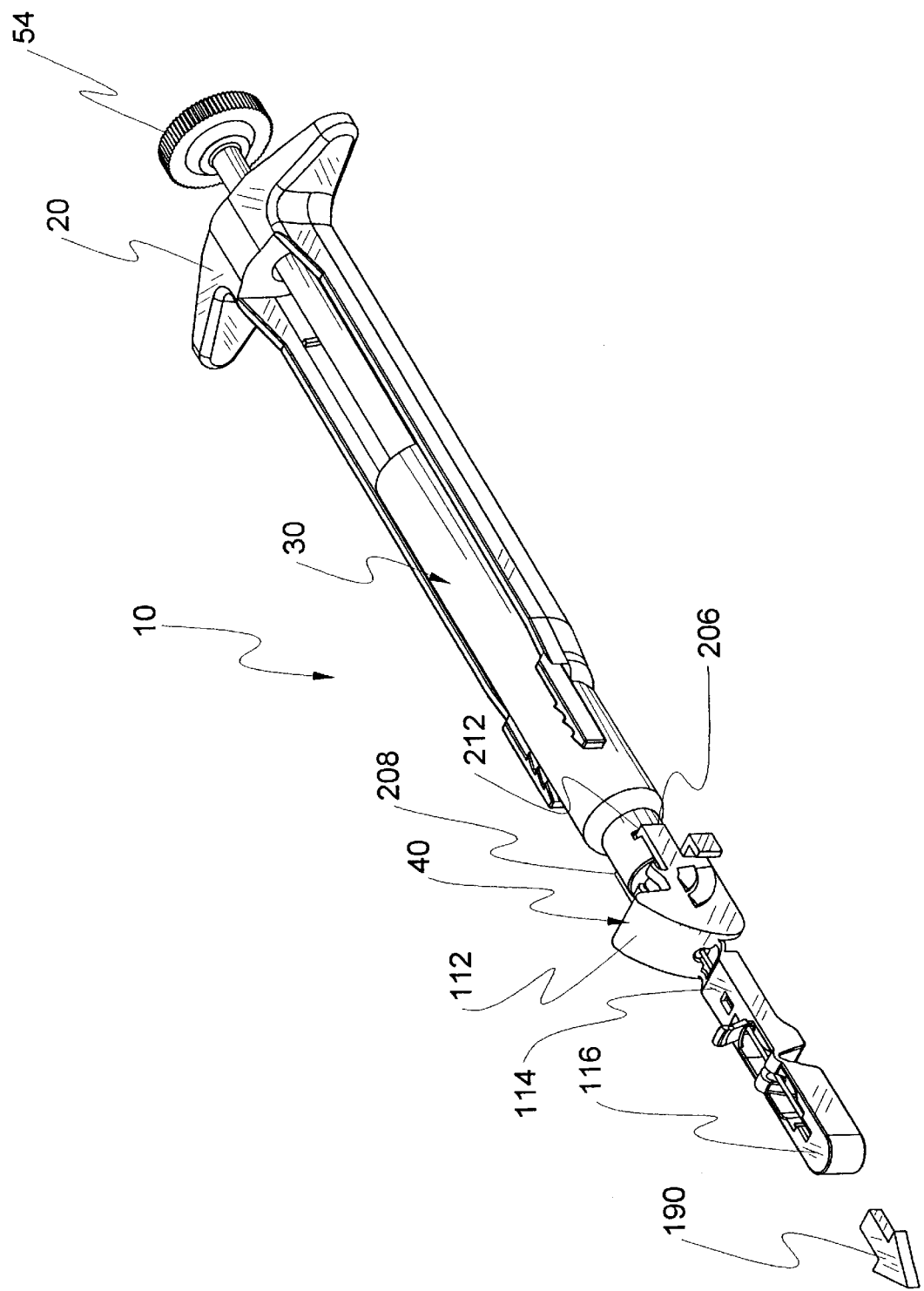
FIG. 12 is a perspective of the device with the needle hub assembly and sterile cartridge partially removed from the holder.

After completion of a medical procedure involving dispensing contents of container 30, needle 50 safety is accomplished by pivoting part 112 relative to holder 20 until sheath parts 112, 114 and 116 are extended and disposed about and enclose needle 50, as seen in FIG. 11. Note that pattern 124 of ratchet teeth 70 is rotated free of arm 60 and therefore of ratchet teeth 70. Such is also the case for the pattern like 124 and associated ratchet 70'. In this manner, as extendable sheath and hub assembly 110 is displaced to sheath needle 50, needle hub assembly 40 and container 30 are disengaged for removal from holder 20, After unthreading plunger rod 54 from plunger 98 (see FIG. 5), container 30 and hub assembly 40 may be disassembled from carrier 20 by linear displacement in the direction of arrow 190 as seen in FIG. 12.

Reference is now made to FIGS. 5, 8, 10 and 12 wherein another safety feature of the invention is depicted. A seen in FIG. 8, A proximal portion 176 of needle 50 comprises sharpened tip 178. While cylindrical section 170 extends to cover tip 178, it may be deemed safer to employ an affixed container 30 to completely cover and protect from any contact with needle tip 178, once contaminated by use.

Distal end 94 of container 30 comprises a bulbous portion 200 extending distally from a comparatively narrow neck 202, provides opportunity to use the distal end as a catch to affix needle hub assembly 40 to a container 30 once needle 50 has been safely shrouded.

For this purpose, as is seen in FIG. 10, face plate 122 comprises an inferior extension 204. Extension 204 comprises a medially disposed latch plate 206. Face plate 122' comprises a similar extension 208 and medially disposed latch plate 210.

Figure 8:
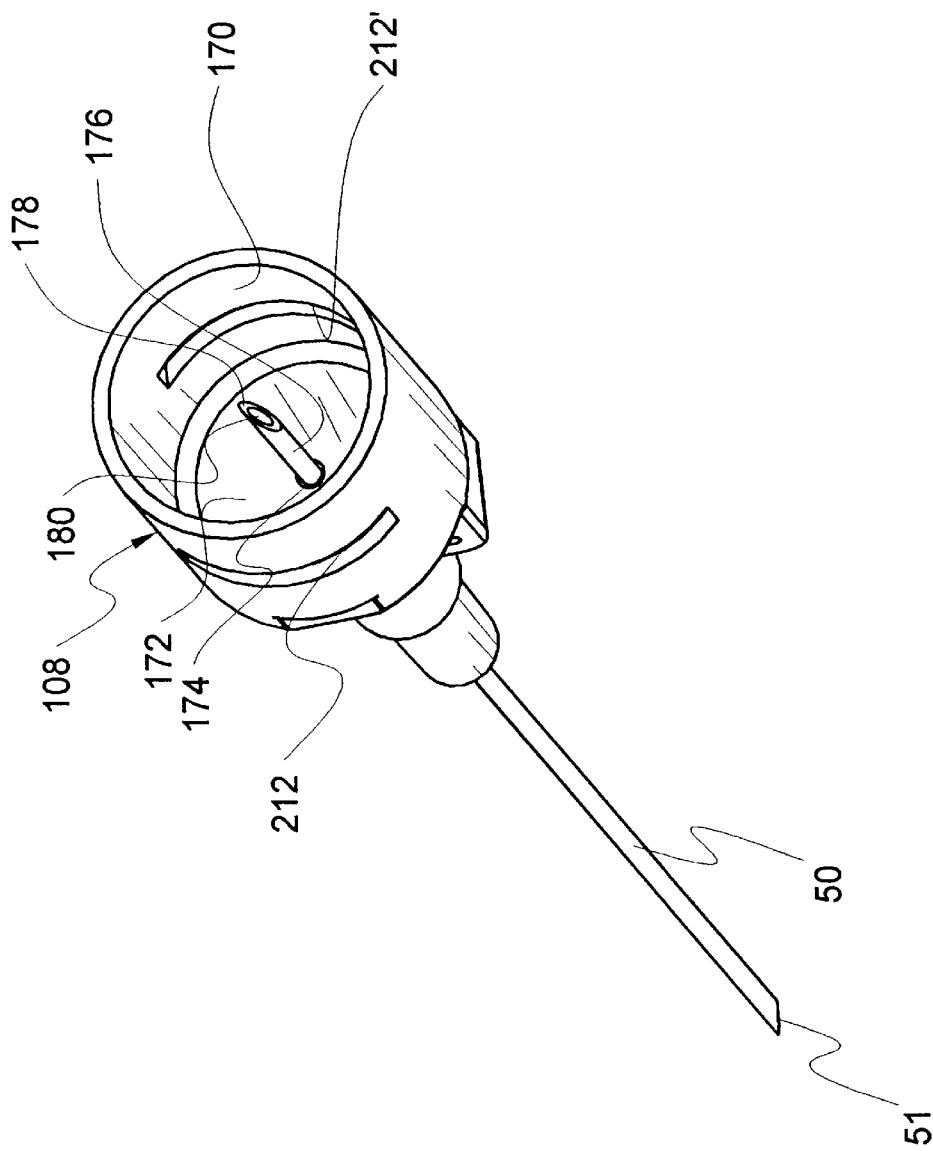
FIG. 8 is a magnified perspective of a needle hub and medical needle portion of the needle hub assembly.

Further, as seen in FIGS. 8 and 10, needle hub 108 comprises a pair of slits 212 and 212'. Slits 212 and 212' are juxtaposed neck 202 of container 30. Extensions 204 and 208 are of appropriate length to cause latch plates 206 and 210 to be displaced into slits 212 and 212', respectively, when part 112 is pivoted to cause needle 50 to be shrouded. Latch plates 206 and 210 are of sufficient length to form a latch catch relationship with bulbous end 202 of container 30. In this manner, when sheath parts 112, 114 and 116 are extended and locked to provide a safety cover for needle 50, latch plates 206 and 210 securely affix container 30 to needle hub assembly 40, as seen in FIG. 12.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A sterile cartridge injector apparatus comprising:
    a sterile cartridge assembly comprising an elongated syringe housing comprising a first end comprising a penetrable seal which, until penetrated, is impermeable to passage of liquids, a second open end disposed opposite said first end, a volume for containing a bolus of dispensable liquid disposed between the first and second ends and a slideable plunger seal disposed between the volume and the second end;
    said plunger seal comprising a releasible attachment whereby a plunger rod is temporarily affixed for use in forcing displacement of the plunger seal through the housing to displace the liquid;
    a sterile cartridge receptacle comprising an elongated cartridge holder wherein said sterile cartridge assembly is reolaceably disposed for use, a proximal end associated with said second open end through which said sterile cartridge assembly is linearly proximally displaceable into the receptacle, said proximal end comprising an abutment which retards proximal displacement of the sterile cartridge assembly toward a user and a distal end associated with said first end;
    the abutment comprising a hole through which the plunger rod communicates with the plunger seal;
    the plunger rod member comprising an elongated stem for communicating with the plunger seal through the hole, a distally disposed connector for releasibly affixing the plunger seal to the releasible attachment and a digital interface for facile displacement of the plunger rod relative to the receptacle;
    the distal end of the sterile cartridge receptacle further comprising at least one distally extending arm which comprises a catch;
    a needle hub assembly comprising:
        a medical needle comprising a proximally disposed sharpened tip for penetrating said seal for access to the bolus of dispensable liquid and a distally disposed sharpened tip for percutaneous entry into a patient;
        a needle hub comprising a latch interface which cooperates with said catch to securely, but releasibly, affix said needle hub assembly to said receptacle for the purpose of retaining the sterile cartridge assembly within the receptacle for the purposes of dispensing liquid therefrom.

2. A sterile cartridge injector and needle hub safety apparatus for a disposable sterile cartridge unit, said apparatus comprising:
    an sterile cartridge injector comprising:
        a sterile cartridge receptacle comprising an elongated cartridge holder wherein a disposable sterile cartridge unit is disposed for use in a medical application, a proximal end comprising an abutment which retards displacement of the sterile cartridge assembly toward a user and a distal end associated with a needle hub assembly;
        a plunger rod, associated with said receptacle, which connectively interfaces with a plunger of the sterile cartridge unit to displace the plunger for the purpose of dispensing fluid from the sterile cartridge unit;
        said distal end comprising a receiving connection whereby said sterile cartridge receptable is securely affixed to the needle hub assembly; and
    the needle hub assembly comprising:
        a medical needle;
        a needle hub in which said needle is securely affixed;
        a displaceable safety sheath securely affixed to said needle hub and disposed to permit access to said medical needle while the needle is used in a medical procedure and displaced and securely latched to provide a protective cover for said medical needle after the procedures;
        an engaging connection comprising a selectively engageable catch which, in combination with said receiving connection, securely affixes said hub assembly to said sterile cartridge receptacle until the displaceable safety sheath is displaced and securely latched to provide the protective cover for the medical needle whereupon the selectively engageable catch is released from engagement with the receiving connection permitting the needle hub assembly to be separated from the sterile cartridge assembly.

3. A sterile cartridge injector and needle hub safety apparatus according to claim 2 wherein said needle hub and said displaceable sheath are formed as a single integrally molded part.

4. A sterile cartridge injector and needle hub safety apparatus according to claim 2 wherein said medical needle comprises a permanent attachment to said needle hub.

5. A sterile cartridge injector and needle hub safety apparatus according to claim 2 wherein said safety sheath comprises a member which pivots about an axis to engage and provide the protective cover for the medical needle.

6. A sterile cartridge injector and needle hub safety apparatus for a disposable sterile cartridge unit, said apparatus comprising:
    a sterile cartridge injector comprising:
        a sterile cartridge receptacle comprising an elongated cartridge holder wherein a disposable sterile cartridge unit is disposed for use in a medical application, a proximal end comprising an abutment which retards displacement of the sterile cartridge unit toward a user and a distal end associated with a needle hub assembly;

a plunger rod, associated with said receptacle, which connectively interfaces with a plunger of the sterile cartridge unit to displace the plunger for the purpose of dispensing fluid from the sterile cartridge unit;

the needle hub safety assembly comprising:
a medical needle;
a needle hub in which said needle is securely affixed;
a displaceable safety sheath securely affixed to said needle hub and disposed to permit access to said medical needle while the needle is used in a medical procedure and displaced and securely latched to provide a protective cover for said medical needle after the procedure, said safety sheath comprising a member which pivots about an axis to engage and provide the protective cover for the medical needle;
said member comprising at least one exterior face which comprises a circular pattern of raised ratchet teeth having a radius of curvature which extends to each tooth from the center of the pivotal axis.

7. A sterile cartridge injector and needle hub safety apparatus according to claim 6 wherein said distal end of said holder comprises at least one distally extending arm comprising a series of ratchet teeth, each series of ratchet teeth cooperating with one of said circular patterns of ratchet teeth to provide a ratchet connector when said sheath is disposed to permit use of said medical needle with a sterile cartridge in a medical procedure, thereby securely, but releasibly, affixing said safety sheath and the medical needle and a sterile cartridge unit, disposed in said holder, to said holder.

8. A sterile cartridge injector and needle hub safety apparatus according to claim 7 wherein said at least one exterior face comprises an area which is void of said pattern and which juxtaposes said series of teeth when said sheath is pivoted to shroud said needle and, thereby, disengaging the ratchet connector.

9. A method for assembling a sterile cartridge into a sterile cartridge injector and needle hub apparatus for use in a medical procedure comprising the steps of:
providing a sterile cartridge unit comprising a bolus of dispensable liquid;
providing the sterile cartridge injector and needle hub apparatus, said apparatus comprising:
a sterile cartridge injector comprising:
a plunger rod which connectively interfaces with a plunger of the sterile cartridge unit plunger;
a sterile cartridge receptacle comprising a cartridge holder having an elongated channel along the long axis of the elongated channel along which said sterile cartridge unit is disposed for use in a medical application, a proximal end comprising an abutment which retards displacement of the sterile cartridge unit toward a user and a distal end associated with a needle hub assembly, said distal end comprising an open channel and a slideably engageable catch;
the needle hub assembly comprising:
a medical needle;
a needle hub in which said needle is securely affixed; and
a slideably engageable latch apparatus which securely, but releasibly, engages said catch apparatus when said needle hub assembly is displaced to be used with said injector, thereby securely affixing the needle hub assembly to the sterile cartridge;
slideably displacing a sterile cartridge in a linear proximal direction into the open channel in parallel with the long axis into said receptacle;
linearly displacing said needle hub assembly latch into contact with said slidably engageable catch to securely affix said cartridge and medical needle in a stable liquid communicating state for use in a medical procedure.

10. A method for assembling a sterile cartridge into a sterile cartridge injector and needle hub apparatus for use in a medical procedure according to claim 9 wherein the sterile cartridge and needle hub apparatus providing step further comprises a step for providing a safety shroud hingeably affixed to said needle hub.

11. A method for assembling a sterile cartridge into a sterile cartridge injector and needle hub apparatus for use in a medical procedure according to claim 10 further comprising pivoting said safety shroud to enclose and protect said needle at the end of a medical procedure.

12. A method for assembling a sterile cartridge into a sterile cartridge injector and needle hub apparatus for use in a medical procedure according to claim 11 wherein said pivoting step includes a step of disengaging said latch from said catch.

13. A combination injector and medical needle hub assembly for a unit-dose sterile cartridge, said combination comprising:
an injector consisting of:
a container tray and holder for a unit-dose sterile cartridge, said container tray and holder comprising a distally disposed open end through which the unit-dose sterile cartridge can be linearly inserted and a similarly disposed, linearly engageable connector whereby a medical needle hub assembly is securely, but releasibly, affixed to the container tray and holder;
a plunger rod disposed to operate in cooperation with said container tray and holder to displace a plunger disposed within the unit-dose sterile cartridge for the purpose of dispensing liquid contents from the unit-dose sterile cartridge;
the medical needle hub assembly comprising:
a medical needle hub;
a medical needle securely affixed to said hub;
a connecting member associated with said medical needle hub which is linearly displaced relative to said container tray and holder to securely, but releasibly, engage said linearly engageable connector for the purpose of affixing the unit-dose sterile cartridge within the combination for use in a medical procedure.

14. A combination injector and medical needle hub assembly for a unit-dose sterile cartridge according to claim 13 wherein said medical needle hub assembly further comprises a safety needle sheath.

15. A combination injector and medical needle hub assembly for a unit-dose sterile cartridge according to claim 14 wherein said safety needle sheath and the connecting member are integrally formed as a single injection molded part.

16. A combination injector and medical needle hub assembly for a unit-dose sterile cartridge according to claim 14 wherein said safety needle sheath comprises a hinged attachment to said medical needle hub by which the sheath is pivoted relative to said medical needle hub assembly, first, to provide a safety sheath for said needle and, second, to disengage and release said member from said linearly engageable connector.

17. A combination injector and medical needle hub assembly for a unit-dose sterile cartridge according to claim 16 further comprising a unit-dose sterile cartridge having a distally disposed coupling and said safety needle sheath comprises a catch for the coupling whereby the safety needle sheath is securely affixed to the unit-dose sterile cartridge when the sheath is pivoted to provide the safety sheath for the medical needle.

18. A combination injector and medical needle hub assembly for a unit-does sterile cartridge according to claim 13 wherein said linearly engageable connector comprises ratchet teeth.

19. An injector for a unit-dose sterile cartridge consisting of:

a container tray and holder for a unit-dose cartridge, said tray and holder comprising a distally disposed open end through which the unit-dose cartridge can be proximally, linearly inserted into the holder and further comprising a linearly engageable connector at said open end whereby a needle hub assembly and a cartridge are securely affixed in the tray for use in a medical procedure;

a plunger rod disposed to operate in cooperation with said container tray to displace a plunger disposed within the so affixed unit-dose sterile cartridge for the purpose of dispensing liquid contents from said cartridge.

20. A needle hub assembly for an associated unit-dose sterile cartridge and a cartridge injector, said needle hub assembly comprising:

a medical needle hub;

a medical needle securely affixed to said hub;

a connecting member integrally affixed to said medical needle hub, said connecting member being linearly displaceable into a receiving connector of an associated cartridge injector to securely, but releasibly, engage and affix said connecting member with the receiving connector to thereby affix the needle hub assembly, an associated but otherwise unsrestrained, liquid containing unit-dose sterile cartridge and the further associated cartridge injector in seriatim for the purpose of dispensing liquid from the unit-dose cartridge through the medical needle.

* * * * *